United States Patent [19]
Bao et al.

[11] Patent Number: 5,800,549
[45] Date of Patent: Sep. 1, 1998

[54] METHOD AND APPARATUS FOR INJECTING AN ELASTIC SPINAL IMPLANT

[75] Inventors: Qi-Bin Bao; Paul A. Higham; Charanpreet S. Bagga; Hansen A. Yuan, all of New York, N.Y.

[73] Assignee: Howmedica Inc., New York, N.Y.

[21] Appl. No.: 846,791

[22] Filed: Apr. 30, 1997

[51] Int. Cl.$^6$ .................... A61F 2/44; A61B 17/56
[52] U.S. Cl. ............................... 623/17; 606/99
[58] Field of Search ..................... 623/17, 16, 66, 623/8; 606/61, 99, 86

[56] References Cited

U.S. PATENT DOCUMENTS

| | | | |
|---|---|---|---|
| 4,545,374 | 10/1985 | Jacobson | 606/61 |
| 4,955,906 | 9/1990 | Coggins et al. | 623/8 |
| 5,439,464 | 8/1995 | Shapiro | 623/17 |
| 5,505,732 | 4/1996 | Michelson | 623/17 |
| 5,571,178 | 11/1996 | Ledergerber | 623/8 |
| 5,645,597 | 7/1997 | Krapiva | 623/17 |

*Primary Examiner*—David Isabella
*Attorney, Agent, or Firm*—Peter C. Richardson; Lawrence C. Akers; Elizabeth O. Slade

[57] ABSTRACT

A method and apparatus for injecting an elastic spinal implant into a cavity in a spinal disc so as to treat disc degeneration are given. The method and apparatus can be used in a variety of surgical approaches with respect to the patient. An elastic spinal nucleus prosthesis is very quickly inserted into the cavity through a small opening in the disc so that permanent deformation of the prosthesis is avoided.

11 Claims, 4 Drawing Sheets

METHOD AND APPARATUS FOR INJECTING AN ELASTIC SPINAL IMPLANT

BACKGROUND OF THE INVENTION

When human vertebral discs degenerate in any of a variety of ways, they can be treated in a variety of ways.

One method of treating disc degeneration is chemical and is commonly referred to as chemonucleolysis. In this method, chymopapain or other enzyme(s) is/are injected within the degenerated disc so as to dissolve tissue. Another method of treating disc degeneration is discectomy, in which some disc material is removed. Also, another method of treating disc degeneration is fusion.

In an alternative method of treating disc degeneration, polymer hydrogel implants have been developed. Such implants are fully disclosed in U.S. Pat. No. 5,047,055 to Bao, which is hereby incorporated herein by reference.

In order to implant such spinal nucleus implants made of hydrogels, some spinal disc tissue must first be removed. Thereafter, the disc implant or implants are then inserted.

One such method for inserting such discs is described in U.S. Pat. No. 5,562,736, assigned to Raymedica. In this method, an incision is made into the spinal disc so as to leave a flap; then the implant is inserted and the flap of the annulus is sewn back into place. This can be done posteriorly with respect to the spine of the patient.

An alternative method for inserting a synthetic spinal nucleus implant was sought.

Objects of this invention are a method and apparatus for inserting a prosthetic spinal disc implant which can be used conveniently, quickly, and safely in the operating room.

Other objects of this invention are a method and apparatus which can be used in various surgical approaches with respect to the patient and which will result in a fast patient recovery and minimized risk of implant extrusion because only a small incision is made in the disc.

Other objects of this invention are a method and apparatus compatible with the surgical instruments which are commonly used in discectomy surgery.

Other objects of this invention are a method and apparatus for very quickly inserting an elastic disc implant, for example that implant disclosed in U.S. Pat. No. 5,047,055 to Bao through a very small annulus opening so that the implant is not permanently deformed.

SUMMARY OF THE INVENTION

These and other objects are satisfied by the insertion device of the invention for inserting an elastic prosthetic spinal nucleus into an intervertebral disc space which device comprises:

(a) a tapered cannula having specific dimensions on the taper; and (b) a force transmitting element for acting on the prosthetic nucleus when the nucleus is positioned within the tapered cannula, the force transmitting element being such that it can inject the prosthetic spinal nucleus through the smaller opening in the cannula at a fast speed (defined below) which avoids permanent deformation of the elastic prosthetic nucleus.

In a preferred embodiment, the force transmitting element is a combination of an incompressible biocompatible fluid and a plunger.

Throughout the following discussion, the terms "proximal" and "distal" are used according to the convention meaning "proximal and distal, respectively, with respect to the patient".

Also according to the invention, a method for implanting an elastic prosthetic nucleus into an intervertebral disc space comprises:

(a) making a small opening in an annulus in the intervertebral disc;

(b) removing a portion of spinal disc tissue; and then (c) inserting into the disc cavity a nucleus implant made of suitable elastic material through a tapered cannula with a specifically dimensioned tapered portion having a straight zone cross-section (A) tapering to an opening having a cross-section (a), with the ratio of A/a being between about 3 and about 8 and at a fast speed which allows the implant to be injected into the disc cavity within a time period lying within the range from about 10 milliseconds to about 5 seconds, the speed being chosen so that permanent deformation of the elastic prosthetic nucleus is avoided.

DESCRIPTION OF THE PREFERRED EMBODIMENTS

DETAILED DESCRIPTION OF THE DRAWINGS

Figure 1:
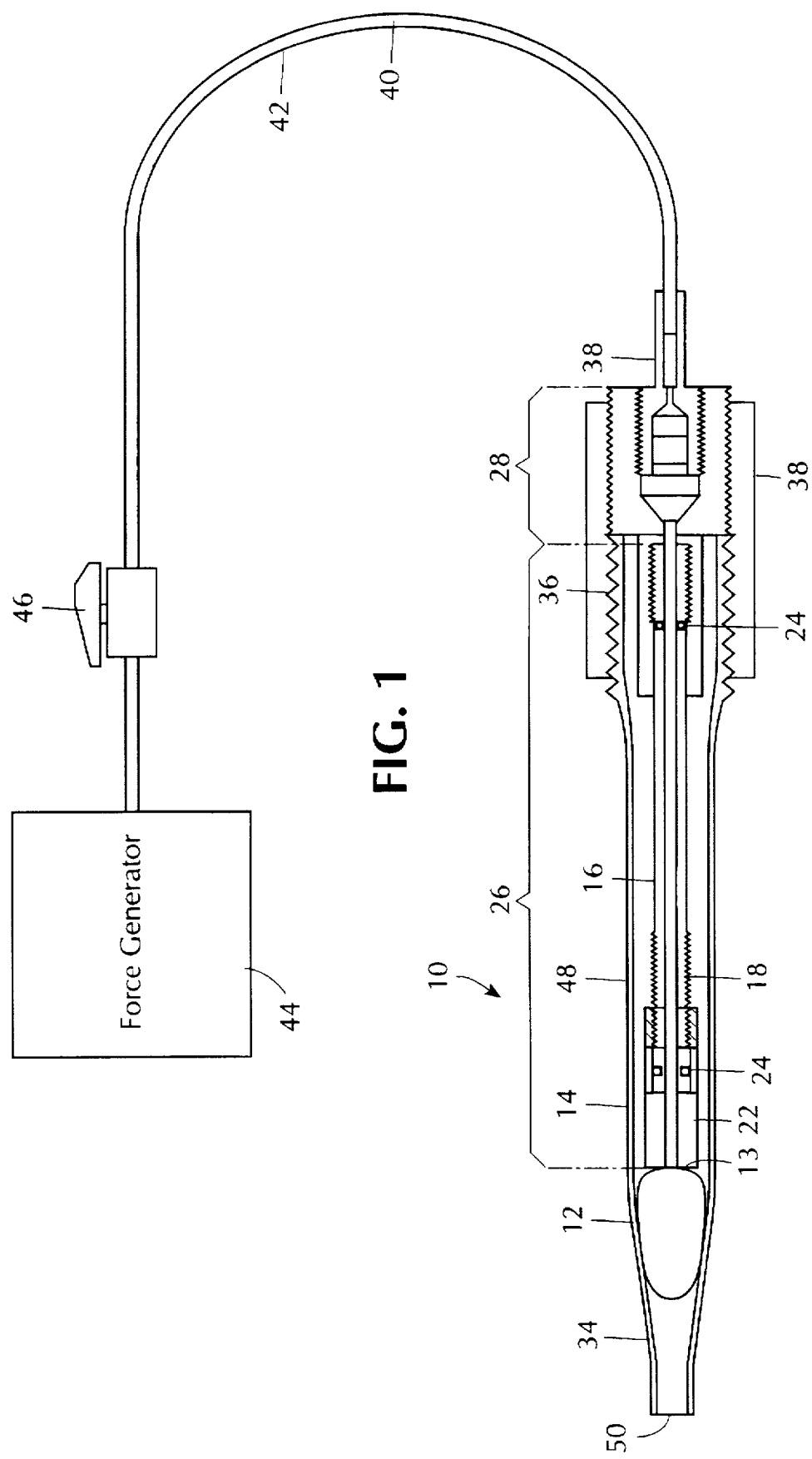
FIG. 1 is a cross-sectional illustration of a tapered cannula of the invention in which a prosthetic spinal nucleus made of elastic material is located within or near the taper of the tapered cannula, and the tapered cannula houses also a force transmitting element which acts on the prosthetic nucleus and which is itself actuated by a force generator (shown schematically).

Referring to the drawing, in FIG. 1, an insertion device (referred to generally as 10) for inserting an elastic prosthetic spinal nucleus 12 into an intervertebral disc space of a human spine is shown partially in cross-section and partially schematically, and comprises a tapered cannula 14 and a force transmitting element 16, which acts upon the elastic prosthetic spinal nucleus 12 located within the tapered cannula 14 so as to eject the elastic prosthetic spinal nucleus 12 from the tapered cannula 14 in a very short time period, further described below. The force transmitting element 16 shown in FIG. 1 in one embodiment is a plunger 18, a part of which is also shown in FIG. 3. In a preferred embodiment, a sealing element 20 which is a combination of a balloon 22 and O-rings is also used.

Plunger 18 is made up of a first portion 26 (shown enlarged in FIGS. 3A, 3B and 3C) and a second portion 28.

Tapered cannula 14 (also shown enlarged in FIG. 2) has a tapered end 34 located at one end thereof and an attachment means 36 located at the other end thereof for attachment of tapered cannula 14 with a coupling 38 (which is a portion of force transmitting element 16).

A conduit 40 houses an incompressible medium 42 therewithin, which in a preferred embodiment is a biocompatible fluid, for example, saline solution. Conduit 40 connects a force generator 44 with force transmitting element 16 and has in a preferred embodiment a valve 46, which can be turned on or off.

Figure 2:
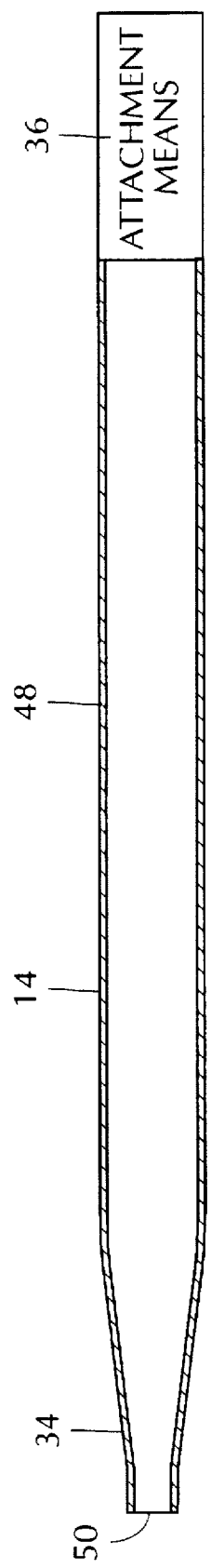
FIG. 2 is a cross-sectional illustration of an embodiment of a tapered cannula for use as part of the device and method of the invention for inserting an elastic prosthetic spinal nucleus into an intervertebral disc space, with an attachment means (shown schematically) for attaching the distal end of the cannula with a force transmitting element.

FIG. 2 is an enlarged view in cross-section of the tapered cannula 14 shown in FIG. 1, with the tapered zone 34 located at one end of tapered cannula 14 and the attachment means 36 located at the opposite end of tapered cannula 14, with a straight zone 48 located therebetween.

Figure 3A:
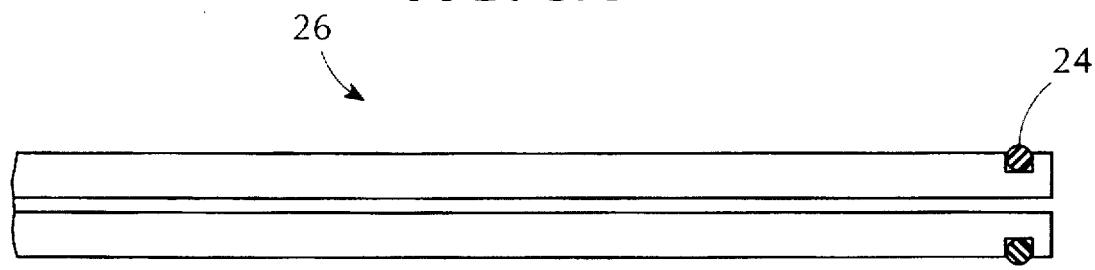
FIG. 3A is a cross-sectional illustration of an embodiment of a portion of a hydraulic plunger, with a sealing element comprising O-rings.

In FIG. 3A, in which first portion 26 of plunger 18 is shown in cross-section, the sealing element 20 comprises O-rings 24.

Figure 3B:
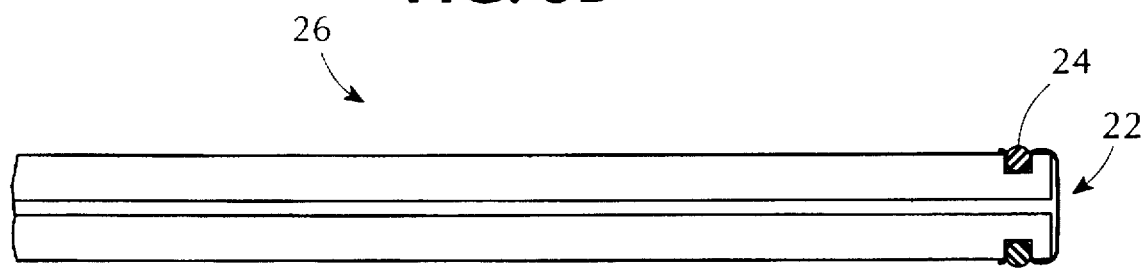
FIG. 3B is a cross-sectional illustration of an embodiment of a portion of a hydraulic plunger in which the sealing element is a balloon.

In FIG. 3B, in which first portion 26 of plunger 18 is shown in cross-section, the sealing element 20 is a balloon 22.

Figure 3C:
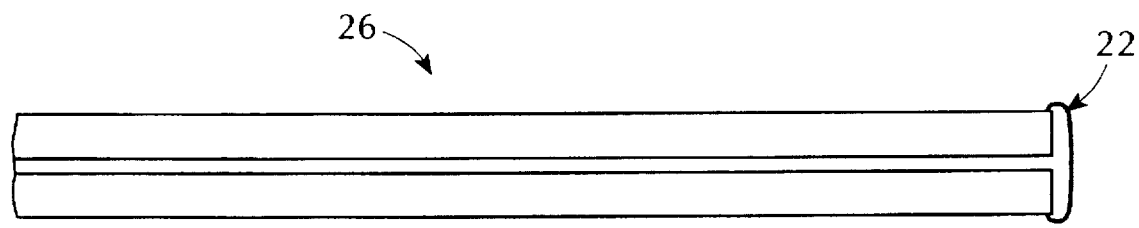
FIG. 3C is a cross-sectional illustration of an embodiment of a portion of a plunger in which the sealing element is a plug or rubber cap located at one end of the plunger and having a hole (not shown) located within the middle of the rubber cap.

In FIG. 3C, in which first portion 26 of plunger 18 is shown in cross-section, the sealing element 20 is a plug or a rubber cap 21 located at the proximal end of first portion 26 of plunger 18, with a hole (not shown) located in the middle of the plug.

Tapered cannula 14 preferably has a shape which is cylindrical, but alternatively, the cross-sectional shape of tapered cannula 14 can be any shape as desired. Tapered cannula 14 has a straight zone 48, one end of which is located adjacent to the attachment means 36 shown in FIG. 2. The cross-sectional area of straight zone 48 approximates the cross-sectional area of the prosthetic spinal nucleus 12 which is to be inserted within tapered cannula 14. Tapered cannula 14 has a tapered zone (or tapered portion) 34 which tapers to a proximal opening 50. The ratio of the cross-sectional area of the straight zone 48 divided by the cross-sectional area of the proximal opening 50 is a ratio within the range from about 3 to about 8.

In a preferred embodiment, the tapered cannula 14 resembles a blow gun (as shown in FIG. 2).

As shown in FIG. 1, the force transmitting element 16 (which is a required element of the apparatus of the invention) first acts on the distal end 13 of the elastic prosthetic spinal nucleus 12 when the nucleus 12 is positioned within the straight zone 48 of the tapered cannula 14. The force transmitting element 16 causes the nucleus 12 first to move into the tapered zone 34 and then out of the proximal opening 50. The force transmitted by the force transmitting element 16 varies directly with the ratio between the cross-sectional area of the straight zone 48 and the cross-sectional area of the proximal opening 50, so that the speed at which the nucleus 12 passes through the proximal opening 50 avoids permanent deformation of the elastic prosthetic nucleus 12.

The force transmitting element 16 can be an incompressible biocompatible medium 42 which pressurizes the tapered cannula 14. In a preferred embodiment, the incompressible biocompatible medium 42 is saline.

Alternatively, the force transmitting element 16 can be a plunger (which is a sliding piece which moves by means of force) like a ram or a piston.

Alternatively, the force transmitting element 16 can be a combination of a plunger and incompressible biocompatible fluid 42.

A force generator 44 will be used to drive the force transmitting element 16.

The force generator 44 can be any suitable type of mechanical (manual or power assisted), gaseous, or hydraulic force generator which is sufficient to provide a speed for the implant 12 to be injected into the disc cavity within a time period within the range from about 10 milliseconds to about 5 seconds.

For example, the force generator 44 can be pressurized air which can be used to drive the incompressible biocompatible medium 42 (the liquid) through a piston. However, air cannot be used as the force transmitting element 16 for the reason that the force transmitting element 16 must be capable of being turned off or stopped after the implant has been injected. This is a required feature of the force transmitting element 16.

In an embodiment wherein the force transmitting element 16 is an incompressible biocompatible medium 42 which pressurizes the tapered cannula 14, the fluid medium 42 should be introduced by a force generator 44 (fluid injection device) which injects between about 3 and about 10 cc of the fluid in less than 5 seconds. When fluid is introduced into the cannula through the plunger, high hydraulic pressure (about 3 to about 10 MPa) is generated within the compartment which is sealed by the elastic nucleus implant and the plunger with a sealing element. A coupling mechanism is needed to lock the plunger to the cannula in order to prevent the plunger from moving backward. This hydraulic pressure creates a high pushing force which ejects the elastic nucleus implant out of the cannula.

The force generator 44 preferably will be used to inject an incompressible medium 42 through the force transmitting element 16. In one embodiment, the force generator 44 can be a manual piston pump sufficient to enable the implant 12 to achieve a speed within the range from about 10 milliseconds to about 1 second. Another suitable type of force generator 44 is a power-assisted pump for driving the plunger 18 or piston. This can be, for example, a ball screw actuator.

Another suitable type of force generator 44 which can be used is a metal spring for forcing the operation of a piston which then acts upon the incompressible medium 42.

A fluid injection volume which is high will have a ballistic effect, due to the flow of high speed liquid. A smaller amount of liquid would not be sufficient to push the implant out of the cannula. In a typical application, the liquid injection volume will be between about 3 and about 10 cubic centimeters.

A sealing element 20 must be used in the practice of the invention as a part of force transmitting element 16 so as to enable sufficient pressure to be built up and then applied to the elastic prosthetic spinal nucleus 12. The sealing element 20 can be a balloon 22, or O-rings 24, or a plug or rubber cap 21, or a combination of a balloon 22 and O-rings 24. A very important requirement in the practice of the invention is to be able to remove all air from the system (i.e., to prime the system).

In the practice of the invention, it is important that the speed at which the elastic prosthetic spinal nucleus 12 passes through the proximal opening 50 be such that the elastic prosthetic nucleus 12 is not permanently deformed. For the elastic materials (further described below) which are useful in the practice of the invention, the speed at which the prosthetic nucleus 12 passes through the proximal opening 50 will generally be within the range from about 10 milliseconds to about 5 seconds.

It is important that the material from which the elastic prosthetic spinal nucleus 12 is formed be able to remember what its original shape was. In the practice of the invention, the elastic prosthetic nucleus implant 12 will be made of a material which is capable of recovering its size and shape after deformation. The material for forming the elastic implant 12 will be chosen such that the implant 12 has only a small amount of deformation, preferably less than about 10 percent.

An example of a suitable elastic material for use in the practice of the invention is an elastomer as defined in U.S. Pat. No. 5,047,055, (Bao), but the elastomer for use in the practice of the invention can be any suitable hydrogel or non-hydrogel or mixture thereof.

The pressure or force required to push the elastic prosthetic spinal nucleus 12 through the tapered cannula 14 must be such that the implant 12 achieves the preferred speed as described above. Therefore, that pressure should be greater than about 3 MPa for an implant of the appropriate size, which is between about 1.5 cc. and about 5 cc. However, the maximum pressure to be used must also take into account the strength of the cannula.

A preferred hydrogel material for use in the practice of the invention is disclosed in Bao, U.S. Pat. No. 5,047,055, and has a water content within the range from about 30 to about 90 weight percent. Most preferably a hydrogel having a water content within the range from about 60 to about 70 weight percent will be used.

One or several pieces of the material of the invention generally will be used, provided that the pieces together form a general shape of the cavity in the disc before the material is compressed.

The amount and type of material to be used in the practice of the invention will be selected such that the implant made therefrom is capable of being compressed into the disc through a small opening in the annulus having a diameter within the range from about 2 to about 6 mm. This diameter will be about the same size as the hole in the disc into which the implant is to be inserted.

In general, if the memory of shape of the material which is used to form the elastic prosthetic spinal nucleus 12 is poor or the stiffness of the material is high, the ratio of the cross-sectional area of the straight zone 48 to the cross-sectional area of the proximal opening 50 must be reduced or the speed of insertion of the implant must be increased by using a larger force. On the other hand, if the memory of shape of the material is good or the stiffness of the material is lower, the ratio of the cross-sectional area (as described above) can be increased or the speed of insertion of the implant 12 can be decreased by using a smaller force.

The inside surface of the tapered cannula 14 should be highly polished or can be coated, if desired, so as to reduce the frictional force between the implant 12 and the tapered cannula 14 and so as to reduce the amount of pressure required to force the implant 12 into the spinal disc. The coating can be either metallic or non-metallic as desired. The tapered cannula 14 must be sufficiently strong so as to withstand the pressure or force used to push the implant 12 into the spinal disc.

A suitable method for implanting an elastic prosthetic spinal nucleus 12 into an intervertebral disc space through a small annulus opening comprises:

(a) making a small opening in the annulus of the disc;

(b) removing a portion of spinal disc tissue; and (c) inserting a nucleus implant made of elastic material through a tapered cannula 14 with a tapered zone 34 tapering to a proximal opening 50, with the ratio of the cross-sectional area of the largest portion of the taper to the cross-sectional area of the distal opening 50 being between about 3 and about 8, and at a sufficiently fast speed so that permanent deformation of the elastic prosthetic nucleus 12 is avoided. Preferably, the speed will be within the range from about 10 milliseconds to about 5 seconds.

Figure 4:
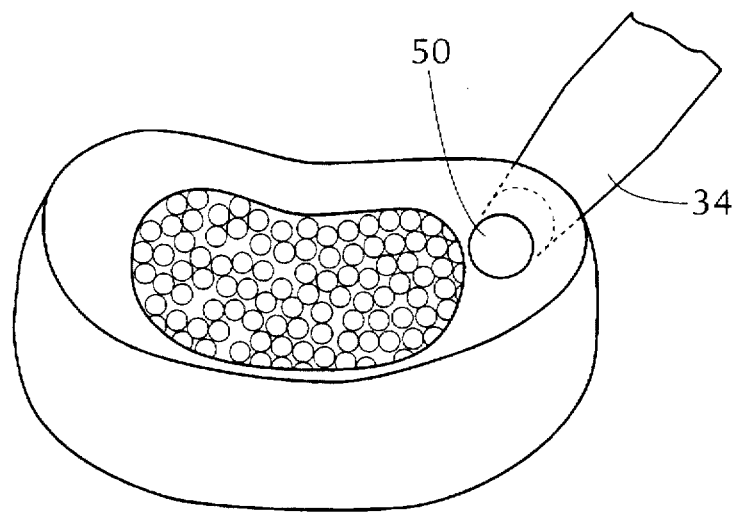
FIG. 4 is a schematic illustration of a tapered cannula which is part of the device of the invention as it is being used for inserting an elastic prosthetic spinal nucleus into an intervertebral disc space in an approach with respect to the patient which is posterior.

In FIG. 4, a schematic illustration of a tapered cannula 14 is shown in a posterior lateral approach with respect to the patient. However, any suitable approach can alternatively be used.

Figure 5:
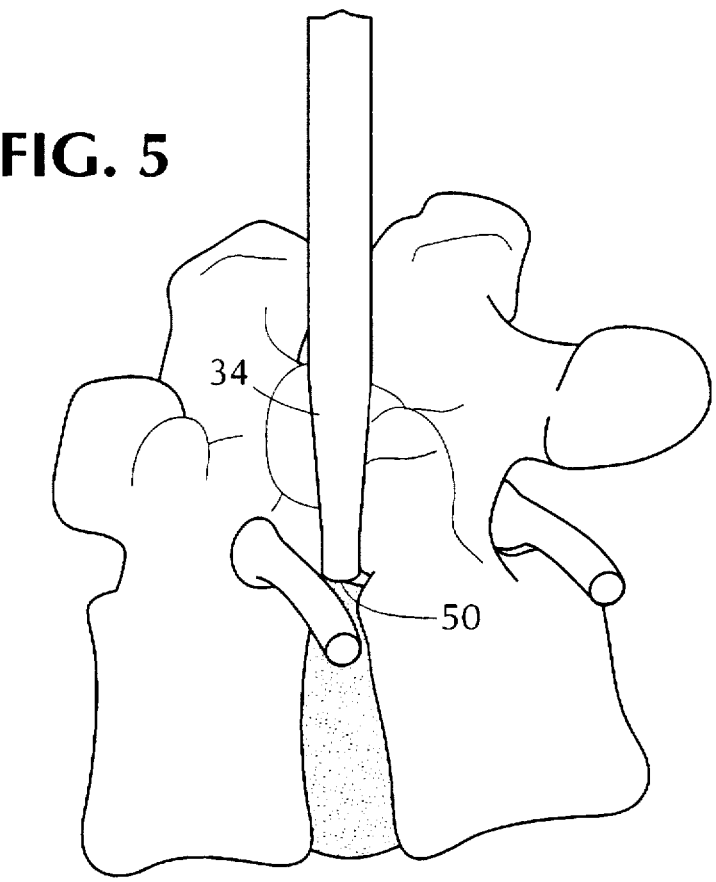
FIG. 5 is a schematic illustration of a tapered cannula which is part of the device of the invention as it is being used for inserting an elastic prosthetic spinal nucleus into an intervertebral disc space in an approach which is posterior with respect to the patient.

In FIG. 5, another schematic illustration of a tapered cannula 14 is shown as it is being used to insert a spinal nucleus implant by means of a tapered cannula in a posterior lateral approach with respect to the patient is illustrated.

EXAMPLE 1

A tapered cannula with a diameter in the straight zone portion of 11.0 mm (cross-sectional area A=95 mm$^2$) and which tapered down to an opening with diameter of 5.0 mm (cross-sectional area a=19.6 mm$^2$) was used to inject four hydrogel nucleus implants of different sizes but with the same water content of 70% (and thus the same bulk modulus or stiffness) and made of the same material which was polyvinyl alcohol and with the same shape, which was cylindrical. The cannula had a ratio of A/a of 4.8. The inner surface of the cannula was coated with Dicronite® (a type of tungsten disulfide) to reduce the frictional force. The injection speed was about 0.5 seconds and was the same for all these four injections. All the variables were held constant except for the size of the implant and the peak pressure needed to inject an implant at the given injection speed of 0.5 seconds. That pressure increased as the implant size increased, as summarized as follows.

| Nucleus Implant Weight (g) | Peak Pressure (MPa) |
| --- | --- |
| 1.81 | 4.14 |
| 2.02 | 5.69 |
| 2.19 | 6.90 |
| 2.47 | 7.59 |

EXAMPLE 2

This example shows that when the ratio of A/a decreased, the peak pressure increased for the same size implant. Two cannulae, both having straight zone diameters of 11 mm but with different tapered opening diameters of 5.0 mm and 4.6 mm, were used for injecting hydrogel nucleus implants of the same size. Both cannulae were coated with Dicronite®, and the A/a ratios were 4.8 for the larger tapered opening and 5.7 for the smaller tapered opening, respectively. The two nucleus implants weighed 2.36 g, had the same water content of 70 w/o, and had the same shape, which was cylindrical.

| A/a | Peak Pressure (MPa) |
|---|---|
| 5.7 | 8.62 |
| 4.8 | 6.55 |

EXAMPLE 3

To investigate how the type of coating reduced the frictional force between the elastic implant and the inner surface of the cannula, two substantially identical cannulae were used. One cannula was coated with Dicronite®, and the other was uncoated. The implants were made of polyvinyl alcohol and had the same size, shape and water content.

| | Peak Pressure (MPa) |
|---|---|
| Dicronite ® coated | 5.69 |
| Uncoated | 7.41 |

We claim:

1. An insertion device for inserting an elastic prosthetic spinal nucleus 12 into an intervertebral disc space, said device comprising:
   (a) a tapered cannula 14 having a straight zone 48 with a cross-sectional area which approximates the cross-sectional area of said prosthetic spinal nucleus 12 and said tapered cannula 14 having a tapered zone 34 which tapers from said straight zone 48 to a proximal opening 50, wherein the cross-sectional area of said straight zone 48 divided by the cross-sectional area of said proximal opening 50 is a ratio lying between about 3 and about 8; and
   (b) a force transmitting element 16 for acting on said elastic prosthetic nucleus 12 at its distal end 13 when said nucleus 12 is positioned within said straight zone 48 of said tapered cannula 14, said force transmitting element 16 causing said nucleus 12 first to move into said tapered zone 34 and then out of said proximal opening 50, the force transmitted by said force transmitting element 16 varying directly with the ratio between the cross-sectional area of said straight zone 48 and the cross-sectional area of said proximal opening 50 so that the speed at which said nucleus 12 passes through said proximal opening 50 is so fast as to avoid permanent deformation of said elastic prosthetic nucleus 12.

2. A device according to claim 1, wherein said force transmitting element 16 is an incompressible biocompatible medium 42 which pressurizes said tapered cannula 14.

3. A device according to claim 2, wherein said medium 42 is saline.

4. A device according to claim 1, wherein said force transmitting element 16 is a plunger.

5. A device according to claim 1, wherein said force transmitting element 16 is a combination of an incompressible biocompatible medium 42 and a plunger 18.

6. A device according to claim 2, and including also a force generator 44 which is a fluid injection device 44 which pressurizes said medium 42 and which injects between about 3 and about 10 cc of said medium 42 in less than 5 seconds so as to generate a pressure greater than about 3 MPa.

7. A device according to claim 1, wherein said force transmitting element 16 includes a sealing element 20 which allows generation of hydraulic pressure when incompressible fluid 42 is injected into said tapered cannula 14 from said force transmitting element 16.

8. A device according to claim 1, wherein said elastic prosthetic spinal nucleus 12 passes through said proximal opening 50 at a speed lying within the range from about 10 milliseconds to about 5 seconds.

9. A method for implanting an elastic prosthetic spinal nucleus 12 into an intervertebral disc space comprises:
   (a) making a small opening in the annulus of said disc;
   (b) removing a portion of spinal disc tissue; and
   (c) inserting a nucleus implant 12 made of elastic material through a tapered cannula 14 with a taper which tapers from a straight zone 48 to a proximal opening 50, with the ratio of the cross-sectional area of straight zone 48 to the cross-sectional area of the proximal opening 50 lying within the range from about 3 to about 8, and at a fast speed so that permanent deformation of said elastic prosthetic nucleus 12 is avoided.

10. A method according to claim 9, wherein said fast speed is within the range from about 10 milliseconds to about 5 seconds.

11. A method according to claim 10, wherein said elastic material is polyvinyl alcohol hydrogel.

* * * * *